US006469001B1

United States Patent
Freyne et al.

(10) Patent No.: US 6,469,001 B1
(45) Date of Patent: Oct. 22, 2002

(54) IL-5 INHIBITING 6-AZAURACIL DERIVATIVES

(76) Inventors: Eddy Jean Edgard Freyne, c/o Janssen Pharmaceutica N.V., Turnhoutseweg 30, B-2340 Beerse (BE); Frederik Dirk Deroose, c/o Janssen Pharmaceutica N.V., Turnhoutseweg 30, B-2340 Beerse (BE); Davy Petrus Franciscus Maria Petit, c/o Janssen Pharmaceutica N.V., Turnhoutseweg, B-2340 Beerse (BE); Jean Fernand Armand Lacrampe, 1 rue Camille Desmoulins, TSA 91003, F-92787 Issy-Les-Moulineaux Cedex 9 (FR)

( * ) Notice: Subject to any disclaimer, the term of this patent is extended or adjusted under 35 U.S.C. 154(b) by 0 days.

(21) Appl. No.: 09/856,625

(22) PCT Filed: Nov. 22, 1999

(86) PCT No.: PCT/EP99/09155

§ 371 (c)(1),
(2), (4) Date: May 22, 2001

(87) PCT Pub. No.: WO00/31054

PCT Pub. Date: Jun. 2, 2000

(30) Foreign Application Priority Data

Nov. 23, 1998 (EP) .............................. 98203930

(51) Int. Cl.[7] .................. C07D 253/075; A61K 31/53; A61P 11/06

(52) U.S. Cl. ................ 514/227.8; 514/235.8; 514/242; 544/182; 544/60; 544/112

(58) Field of Search .............. 544/182, 60, 112; 514/242, 227.8, 235.8

(56) References Cited

FOREIGN PATENT DOCUMENTS

| EP | 0 831 088 | 3/1998 |
|---|---|---|
| WO | WO 99/02504 | 1/1999 |

Primary Examiner—Richard L. Raymond
Assistant Examiner—Venkataraman Balasubramanian
(74) Attorney, Agent, or Firm—Matt Zisk

(57) ABSTRACT

The present invention is concerned with the compounds of formula

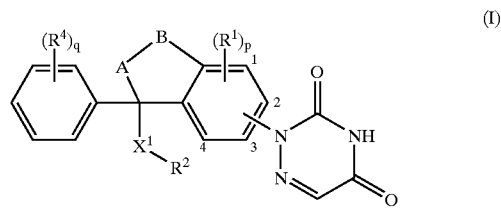

(I)

the N-oxides, the pharmaceutically acceptable addition salts and the stereochemically isomeric forms thereof, wherein p is 0 to 3; q is 0 to 5; —A—B— is —$(CH_2)_r$—, —$(CH_2)_r$—O—, —$(CH_2)_t$—S(=O)$_u$— or —$(CH_2)_t$—$NR^3$—; r is 2 to 4; t is 1 to 3; u is 0 to 2; $X^1$ is O, S, $NR^3$ or a direct bond; $R^1$ and $R^4$ are $C_{1-6}$alkyl, halo, polyhalo $C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $Het^3$, $R^6$ or $NR^7R^8$; $R^2$ represents aryl, $Het^1$, $C_{3-7}$cycloalkyl, cyano, $C_{1-6}$alkyl, —C(=Q)—$X^2$—$R^{15}$ or $C_{1-6}$alkyl substituted with one or two substituents selected from hydroxy, cyano, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$ oxy, $Het^1$ thio and —C(=Q)—$X^2$—$R^{15}$; $R^3$ is hydrogen or $C_{1-4}$alkyl; $R^{15}$ is hydrogen, optionally substituted $C_{1-6}$alkyl, $C_{3-7}$cycloalkyl, aryl; where $X^2$ is a direct bond, $R^{15}$ is also halo or $Het^1$; where $X^2$ is $NR^5$, $R^{15}$ is also hydroxy; where $X^2$ is C(=O)—NH—NH or NH—NH—C(=O), $R^{15}$ is replaced by $R^{11}$; $R^5$ is hydrogen, $C_{1-6}$alkyl, $C_{1-6}$alkyloxy or aryl$C_{1-6}$alkyl; Q is O, S or $NR^3$; $X^2$ is O, S, $NR^5$, C(=O)—NH—NH, NH—NH—C(=O) or a direct bond; $R^6$ is a sulfonyl or sulfinyl derivative; $R^7$ and $R^8$ are independently hydrogen, optionally substituted $C_{1-4}$alkyl, aryl, a carbonyl containing moiety, $C_{3-7}$cycloalkyl, —Y—$C_{1-4}$alkanediyl—C(=O)—O—$R^{14}$, $Het^3$ and $R^6$; $R^{11}$ is hydroxy, mercapto, cyano, nitro, halo, trihalomethyl, $C_{1-4}$alkyloxy, formyl, trihalo$C_{1-4}$alkylsulfonyloxy, $R^6$, $NR^7R^8$, C(=O)$NR^7R^8$, $C_{1-4}$alkanediyl—C(=O)—O—$R^{14}$, —C(=O)—O—$R^{14}$,. —Y—$C_{1-4}$alkanediyl—C(=O)—O—$R^{14}$, aryl, aryloxy, arcarbonyl, $C_{3-7}$cycloalkyl, $C_{3-7}$cycloalkyloxy, phthalimide-2-yl, $Het^3$, $Het^4$ and C(=O)$Het^3$; aryl is optionally substituted phenyl; $Het^1$, $Het^2$, $Het^3$ and $Het^4$ are optionally substituted heterocycles; to processes for their preparation and compositions comprising them. It further relates to their use as a medicine.

8 Claims, No Drawings

IL-5 INHIBITING 6-AZAURACIL DERIVATIVES

CROSS REFERENCE TO RELATED APPLICATIONS

This application is a National Stage application under 35 U.S.C. 371 of PCT/EP99/09155 filed Nov. 22, 1999, which claims priority from EP 98.203.930.7, filed Nov. 23, 1998.

The present invention concerns IL-5 inhibiting 6-azauracil derivatives useful for treating eosinophil-dependent inflammatory diseases; to processes for their preparation and compositions comprising them. It further relates to their use as a medicine.

Eosinophil influx, leading to subsequent tissue damage, is an important pathogenic event in bronchial asthma and allergic diseases. The cytokine interleukin-5 (IL-5), produced mainly by T lymphocytes as a glycoprotein, induces the differentiation of eosinophils in bone marrow and, primes eosinophils for activation in peripheral blood and sustains their survival in tissues. As such, IL-5 plays a critical role in the process of eosinophilic inflammation. Hence, the possibility that inhibitors of IL-5 production would reduce the production, activation and/or survival of eosinophils provides a therapeutic approach to the treatment of bronchial asthma and allergic diseases such as, atopic dermatitis, allergic rhinitis, allergic conjunctivitis, and also other eosinophil-dependent inflammatory diseases.

Steroids, which strongly inhibit IL-5 production ill vitro, have long been used as the only drugs with remarkable efficacy for bronchial asthma and atopic dermatitis, but they cause various serious adverse reactions such as diabetes, hypertension and cataracts. Therefore, it would be desirable to find non-steroidal compounds having the ability to inhibit IL-5 production in human T-cells and which have little or no adverse reactions.

U.S. Pat. No. 4,631,278 discloses α-aryl-4-(4,5-dihydro-3,5-dioxo-1,2,4-triazin-2(3H)-yl)-benzeneacetonitriles and U.S. Pat. No. 4,767,760 discloses 2-(substituted phenyl)-1,2,4-triazine-3,5(2H,4H)-diones, all having anti-protozoal activity, in particular, anti-coccidial activity. EP 831,088 discloses 1,2,4-triazine-3,5-diones as anticoccidial agents. Unexpectedly, the 6-azauracil derivatives of the present invention prove to be potent inhibitors of the production of IL-5.

The present invention is concerned with the compounds of formula

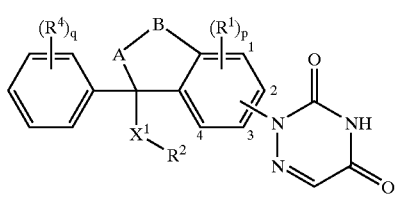

(I)

the N-oxides, the pharmaceutically acceptable addition salts and the stereochemically isomeric forms thereof, wherein:

p represents an integer being 0, 1, 2 or 3;
q represents an integer being 0, 1, 2, 3, 4 or 5;
—A—B— represents —$(CH_2)_r$—, —$(CH_2)_r$—O—, —$(CH_2)_r$—S(=O)$_u$— or —$(CH_2)_r$—NR$^3$—;
r represents 2, 3 or 4;
each t independently represents 1, 2 or 3;
u represents 0, 1 or 2;

$X^1$ represents O, S, NR$^3$ or a direct bond;
each R$^1$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, Het$^3$, R$^6$, NR$^7$R$^8$ or $C_{1-4}$alkyl substituted with Het$^3$, R$^6$ or NR$^7$R$^8$;
R$^2$ represents aryl, Het$^1$, $C_{3-7}$cycloalkyl, cyano, $C_{1-6}$alkyl, —C(=Q)—X$^2$—R$^{15}$ or $C_{1-6}$alkyl substituted with one or two substituents selected from hydroxy, cyano, amino, mono-or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, Het$^1$, Het$^1$Het$^1$thio and —C(=Q)—X$^2$—R$^{15}$;
R$^3$ represents hydrogen or $C_{1-4}$alkyl;
each R$^4$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, Het$^3$, R$^6$,
NR$^7$R$^8$ or $C_{1-4}$alkyl substituted with Het$^3$, R$^6$ or NR$^7$R$^8$;
each R$^{15}$ independently represents hydrogen, $C_{1-6}$alkyl, $C_{3-7}$cycloalkyl, aryl or $C_{1-6}$alkyl substituted with aryl, halo, hydroxy or Het$^1$;
where X$^2$ is a direct bond, R$^{15}$ may also be halo or Het$^1$;
where X$^2$ is NR$^5$, R$^{15}$ may also be hydroxy;
where X$^2$ is C(=O)—NH—NH or NH—NH—C(=O), R$^{15}$ may be replaced by R$^{11}$; R$^5$ represents hydrogen, $C_{1-6}$alkyl, $C_{1-6}$alkyloxy or aryl$C_{1-6}$alkyl;
each Q independently represents O, S or NR$^3$;
each X$^2$ independently represents O, S, NR$^5$, C(=O)—NH—NH, NH—NH—C(=O) or a direct bond;
each R$^6$ independently represents $C_{1-6}$alkylsulfonyl, aminosulfonyl, mono- or di-($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl $C_{1-4}$alkylsulfonyl, piperazinylsulfonyl, aminopiperidinylsulfonyl, piperidinylaminosulfonyl, N—$C_{1-4}$alkyl—N-piperidinylaminosulfonyl or mono- or di($C_{1-4}$alkyl)amino$C_{1-4}$alkylsulfonyl;
each R$^7$ and each R$^8$ are independently selected from hydrogen, $C_{1-4}$alkyl, hydroxy-$C_{1-4}$alkyl, dihydroxy $C_{1-4}$alkyl, aryl, aryl$C_{1-4}$alkyl, $C_{1-4}$alkyloxy$C_{1-4}$alkyl, $C_{1-4}$alkylcarbonyl, aminocarbonyl, arylcarbonyl, Het$^3$carbonyl, $C_{1-4}$alkylcarbonyloxy-$C_{1-4}$alkylcarbonyl, hydroxy$C_{1-4}$alkylcarbonyl, $C_{1-4}$alkyloxycarbonylcarbonyl, mono- or di($C_{1-4}$alkyl)amino$C_{1-4}$alkyl, arylaminocarbonyl, arylaminothiocarbonyl, Het$^3$aminocarbonyl, Het$^3$aminothiocarbonyl, $C_{3-7}$cycloalkyl, pyridinyl $C_{1-4}$alkyl, $C_{1-4}$alkanediyl-C(=O)—O—R$^{14}$, —C(=O)—O—R$^{14}$, —Y—$C_{1-4}$alkanediyl-C(=O)—O—R$^{14}$, Het$^3$ and R$^6$;
Y represents O, S, NR$^3$, or S(O)$_2$;
R$^9$ and R$^{10}$ are each independently selected from hydrogen, $C_{1-4}$alkyl, hydroxy$C_{1-4}$alkyl, dihydroxy $C_{1-4}$alkyl, phenyl, phenyl$C_{1-4}$alkyl, $C_{1-4}$alkyloxy $C_{1-4}$alkyl, $C_{1-4}$alkylcarbonyl, aminocarbonyl, phenylcarbonyl, Het$^3$carbonyl, $C_{1-4}$alkylcarbonyloxy-$C_{1-4}$alkylcarbonyl, hydroxy$C_{1-4}$alkylcarbonyl, $C_{1-4}$alkyloxycarbonylcarbonyl, mono-or di($C_{1-4}$alkyl)amino$C_{1-4}$alkyl, phenylaminocarbonyl, phenylaminothiocarbonyl, Het$^3$aminocarbonyl, Het$^3$aminothiocarbonyl, $C_{3-7}$cycloalkyl, pyridinyl $C_{1-4}$alkyl, $C_{1-4}$alkanediyl—C(=O)—O—R$^{14}$, —C(=O)—O—R$^{14}$, —Y—$C_{1-4}$alkanediyl—C(=O)—O—R$^{14}$, Het$^3$ and R$^6$;

each $R^{11}$ independently being selected from hydroxy, mercapto, cyano, nitro, halo, trihalomethyl, $C_{1-4}$alkyloxy, formyl, trihalo$C_{1-4}$alkylsulfonyloxy, $R^6$, $NR^7R^8$, $C(=O)NR^7R^8$, $—C(=O)—O—R^{14}$, $—Y—C_{1-4}$alkanediyl$—C(=O)—O—R^{14}$, aryl, aryloxy, arylcarbonyl, $C_{3-7}$cycloalkyl, $C_{3-7}$cycloalkyloxy, phthalimide-2-yl, $Het^3$, $Het^4$ and $C(=O)Het^3$;

$R^1$ and $R_2$ are each independently selected from hydrogen, $C_{1-4}$alkyl, hydroxy$C_{1-4}$alkyl, dihydroxy $C_{1-4}$alkyl, phenyl, phenyl$C_{1-4}$alkyl, $C_{1-4}$alkyloxy $C_{1-4}$alkyl, $C_{1-4}$alkylcarbonyl, phenylcarbonyl, $C_{1-4}$alkylcarbonyloxy$C_{1-4}$alkylcarbonyl, hydroxy $C_{1-4}$alkylcarbonyl, $C_{1-4}$alkyloxycarbonylcarbonyl, mono- or di($C_{1-4}$alkyl)amino$C_{1-4}$alkyl, phenylaminocarbonyl, phenylaminothiocarbonyl, $C_{3-7}$cycloalkyl, pyridinyl$C_{1-4}$alkyl, $C_{1-4}$alkanediyl$—C(O)—O—R^{14}$, $—C(=O)—O—R^{14}$, $—Y—C_{1-4}$alkanediyl-$C(=O)—O—R^{14}$ and $R^6$;

each $R^{14}$ independently represents hydrogen, $C_{1-4}$alkyl, $C_{3-7}$cycloalkyl, aminocarbonylmethylene, mono-or di($C_{1-4}$alkyl)aminocarbonylmethylene, mono-or di($C_{3-7}$cycloalkyl)aminocarbonylmethylene, azetidin-1-ylcarbonylmethylene, pyrrolidin-1-ylcarbonylmethylene, piperidin-1-ylcarbonylmethylene or homopiperidin-1-ylcarbonylmethylene;

aryl represents phenyl optionally substituted with one, two or three substituents each independently selected from nitro, azido, cyano, halo, hydroxy, $C_{1-4}$alkyl, $C_{3-7}$cyclo-alkyl, $C_{1-4}$alkyloxy, formyl, polyhalo $C_{1-4}$alkyl, $NR^9R^{10}$, $C(=O)NR^9R^{10}$, $C(=O)—O—R^{14}$, $R^6$, $—O—R^6$, phenyl, $Het^3$, $C(=O)Het^3$ and $C_{1-4}$alkyl substituted with hydroxy, $C_{1-4}$alkyloxy, $C(=O)—O—R^{14}$, $—Y—C_{1-4}$alkanediyl-$C(=O)—O—R^{14}$, $Het^3$ or $NR^9R^{10}$;

$Het^1$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $Het^2$, $R^{11}$ and $C_{1-4}$alkyl optionally substituted with one or two substituents independently selected from $Het^2$ and $R^{11}$;

$Het^2$ represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from $R^{11}$ and $C_{1-4}$alkyl optionally substituted with one or two substituents independently selected from $R_{11}$;

$Het^3$ represents a monocyclic heterocycle selected from pyrrolidinyl, piperidinyl, piperazinyl, morpholinyl, thiomorpholinyl and tetrahydropyranyl; wherein said monocyclic heterocycles each independently may optionally be substituted with, where possible, one, two, three or four substituents each independently selected from hydroxy, $C_{1-4}$alkyl, $C_{1-4}$alkyloxy, $C_{1-4}$alkylcarbonyl, piperidinyl, $NR^{12}R^{13}$, $C(=O)—O—R^{14}$, $R^6$ and $C_{1-4}$alkyl substituted with one or two substituents independently selected from hydroxy, $C_{1-4}$alkyloxy, phenyl, $C(=O)—O—R^{14}$, $—Y—C_{1-4}$alkanediyl—$C(=O)—O—R^{14}$, $R^6$ and $NR^{12}R^{13}$;

$Het^4$ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl.

As used in the foregoing definitions and hereinafter, halo is generic to fluoro, chloro, bromo and iodo; $C_{3-7}$cycloalkyl is generic to cyclopropyl, cyclobutyl, cyclopentyl, cyclohexyl and cycloheptyl; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-6}$alkyl is meant to include $C_{1-4}$alkyl and the higher homologues thereof having 5 or 6 carbon atoms such as, for example, pentyl, 2-methylbutyl, hexyl, 2-methylpentyl and the like; polyhalo$C_{1-4}$alkyl is defined as polyhalosubstituted $C_{1-4}$alkyl, in particular $C_{1-4}$alkyl substituted with 1 to 6 halogen atoms, more in particular difluoro- or trifluoromethyl; polyhalo$C_{1-6}$alkyl is defined as polyhalosubstituted $C_{1-6}$alkyl. The term $C_{1-4}$alkanediyl defines bivalent straight or branch chained alkanediyl radicals having from 1 to 4 carbon atoms such as, for example, methylene, 1,2-ethanediyl, 1,3-propanediyl, 1,4-butanediyl and the like; $C_{2-6}$alkanediyl defines bivalent straight or branch chained alkanediyl radicals having from 2 to 6 carbon atoms such as, for example, 1,2-ethanediyl, 1,3-propanediyl, 1,4-butanediyl, 1,5-pentanediyl, 1,6-hexanediyl and the like.

$Het^1$, $Het^2$, $Het^3$ and $Het^4$ are meant to include all the possible isomeric forms of the heterocycles mentioned in the definition of $Het^1$, $Het^2$, $Het^3$ and $Het^4$, for instance, pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

The heterocycles represented by $Het^1$, $Het^2$, $Het^3$ and $Het^4$ may be attached to the remainder of the molecule of formula (I) through any ring carbon or heteroatom as appropriate. Thus, for example, when the heterocycle is imidazolyl, it may be a 1-imidazolyl, 2-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzthiazolyl, it may be 2-benzthiazolyl, 4-benzthiazolyl, 5-benzthiazolyl, 6-benzthiazolyl and 7-benzthiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide. For example, one or more nitrogen atoms of any of the heterocycles in the definition of $Het^1$, $Het^2$ and $Het^3$ may be N-oxidized.

Some of the compounds of formula (I) may also exist in their tautomeric forms. Such forms although not explicitly indicated in the above formula are intended to be included within the scope of the present invention. For example, a hydroxy substituted triazine moiety may also exist as the corresponding triazinone moiety; a hydroxy substituted pyrimidine moiety may also exist as the corresponding pyrimidinone moiety.

The term "stereochemically isomeric forms" as used hereinbefore defines all the possible stereoisomeric forms in which the compounds of formula (I) can exist. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration, used herein in accordance with Chemical Abstracts nomenclature. Stereochemically isomeric forms of the compounds of formula (I) are obviously intended to be embraced within the scope of this invention.

The compounds of formula (I) and some of the intermediates in the present invention contain one or more asymmetric carbon atoms. The pure and mixed stereochemically isomeric forms of the compounds of formula (I) are intended to be embraced within the scope of the present invention.

Whenever used hereinafter, the term "compounds of formula (I)" is meant to also include their N-oxide forms, their pharmaceutically acceptable addition salts, and their stereochemically isomeric forms.

An interesting group of compounds are those compounds of formula (I) wherein the 6-azauracil moiety is connected to the annelated phenyl ring in the 2 or 3 position; preferably in the 2 position.

Another interesting group contains those compounds of formula (I) wherein one or more of the following restrictions apply:

p is 0, 1 or 2, preferably p is 0;

q is 0 or 1;

$X^1$ is S, $NR^3$ or a direct bond; more in particular a direct bond;

each $R^1$ independently is halo, polyhalo$C_{1-6}$alkyl, $C_{1-6}$alkyl, $C_{1-6}$alkyloxy or aryl, preferably $R^1$ is chloro;

$R^2$ is $Het^1$, cyano, —C(=Q)—$X^2$—$R^{15}$ or $C_{1-6}$alkyl substituted with one or two substituents selected from hydroxy, cyano, —C(=Q)—$X^2$—$R^{15}$, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$oxy and $Het^1$thio; more in particular $Het^1$, cyano or —C(=Q)—$X^2$—$R^{15}$;

each $R^4$ independently represents $C_{1-6}$alkyl, halo, polyhalo$C_{1-6}$alkyl, $R^6$ or $C_{1-6}$alkyloxy;

$R^{15}$ is hydrogen or $C_{1-6}$alkyl, and when $X^2$ is a direct bond, $R^{15}$ may also be halo, and when $X^2$ is C(=O)—NH—NH, $R^{15}$ may also be phenyl;

$R^6$ is $C_{1-6}$alkylsulfonyl or aminosulfonyl;

$R^7$ and $R^8$ are each independently hydrogen, $C_{1-4}$alkyl, $Het^3$ or $R^6$;

$R^9$ and $R^{10}$ are each independently hydrogen, $C_{1-4}$alkyloxy$C_{1-4}$alkyl, $C_{1-4}$alkylcarbonyl, aminocarbonyl, $Het^3$carbonyl, $Het^3$ or $R^6$;

$R^{11}$ is cyano, nitro, halo, $C_{1-4}$alkyloxy, formyl, $NR^7R^8$, $C(=O)NR^7R^8$, —C(=O)—O—$R^{14}$, aryl, arylcarbonyl, $Het^3$, $Het^4$ and C(=O)$Het^3$, more in particular aryl, —C(=O)—O—$R^{14}$, $R^{14}$ is hydrogen or $C_{1-4}$alkyl;

aryl is phenyl optionally substituted with one, two or three substituents each independently selected from nitro, cyano, halo, hydroxy, $C_{1-4}$alkyl, $C_{3-7}$cycloalkyl, $C_{1-4}$alkyloxy, formyl, polyhalo$C_{1-4}$alkyl, $NR^9R^{10}$, C(=O)$NR^9R^{10}$, C(=O)—O—$R^{14}$, —O—$R^6$, phenyl, C(=O)$Het^3$ and $C_{1-4}$alkyl substituted with hydroxy, $C_{1-4}$alkyloxy, C(=O)—O—$R^{14}$, $Het^3$ or $NR^9R^{10}$, more in particular phenyl optionally substituted with halo or $C_{1-4}$alkyl;

$Het^1$ is a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl, in particular imidazolyl, oxadiazolyl, thiazolyl, pyrimidinyl or pyridinyl, wherein said monocyclic heterocycles each independently may optionally be substituted with one, or where possible, two or three substituents each independently selected from Het$^2$, R$^{11}$ and C$_{1-4}$alkyl optionally substituted with Het$^2$ or R$^{11}$; preferably Het$^1$ is oxadiazolyl or thiazolyl each independently and optionally substituted with one, or where possible, two or three substituents each independently selected from R$^{11}$ and C$_{1-4}$alkyl optionally substituted with R$^{11}$;

Het$^2$ is an aromatic heterocycle; more in particular furanyl, thienyl, pyridinyl or benzothienyl, wherein said aromatic heterocycles each independently may optionally be substituted with one, or where possible, two or three substituents each independently selected from R$^{11}$ and C$_{1-4}$alkyl;

Het$^3$ is piperidinyl, piperazinyl, morpholinyl and tetrahydropyranyl each independently and optionally substituted with, where possible, one, two, three or four substituents each independently selected from hydroxy, C$_{1-4}$alkyl, C$_{1-4}$alkylcarbonyl, piperidinyl and C$_{1-4}$alkyl substituted with one or two substituents independently selected from hydroxy, C$_{1-4}$alkyloxy and phenyl;

Het$^4$ is thienyl.

Special compounds are those compounds of formula (I) wherein p is 0, 1 or 2 and each R$^1$ is chloro; preferably p is 0.

Particular compounds are those compounds of formula (I) wherein the 6-azauracil moiety is in the 2 position, and p is 0.

Other particular compounds are those compounds of formula (I) wherein X$^1$ is a direct bond and R$^2$ is cyano or a monocyclic heterocycle selected from thiazolyl and oxadiazolyl, wherein said monocyclic heterocycles each independently may optionally be substituted with one or two substituents each independently selected from R$_{11}$ and C$_{1-4}$alkyl optionally substituted with R$^{11}$.

Preferred compounds are those compounds of formula (I) wherein —A—B— is (CH$_2$)$_r$; more preferably (CH$_2$)$_2$.

More preferred compounds are those compounds of formula (I) wherein —X$^1$—R$^2$ is optionally substituted 2-thiazolyl or 3-oxadiazolyl, the 6-azauracil moiety is in the 2 position, and p is 0.

In order to simplify the structural representation of the compounds of formula (I), the group

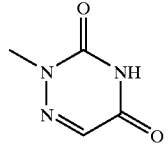

will hereinafter be represented by -AZA.

Compounds of formula (I) can generally be prepared by reacting an intermediate of formula (II) wherein W$^1$ is a suitable leaving group such as, for example, a halogen atom, with an appropriate reagent of formula (III).

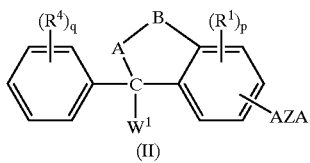 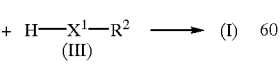

Said reaction may be performed in a reaction-inert solvent such as, for example, acetonitrile, N,N-dimethylformamide, acetic acid, tetrahydrofuran, ethanol or a mixture thereof.

Alternatively, in case the reagent of formula (III) acts as a solvent, no additional reaction-inert solvent is required. The reaction is optionally carried out in the presence of a base such as, for example, 1,8-diazabicyclo[5.4.0]undec-7-ene, sodium bicarbonate, sodiummethanolate and the like. Convenient reaction temperatures range between −70° C. and reflux temperature.

In this and the following preparations, the reaction products may be isolated from the reaction medium and, if necessary, further purified according to methodologies generally known in the art such as, for example, extraction, crystallization, distillation, trituration and chromatography.

Some of the compounds and intermediates of the present invention can be prepared according to or analogous to the procedures described in EP-A-0,170,316, EP-A-0,232,932 and PCT/EP98/04191.

For instance, compounds of formula (I) may generally be prepared by cyclizing an intermediate of formula (IV) wherein L is a suitable leaving group such as, for example, C$_{1-6}$alkyloxy or halo, and E represents an appropriate electron attracting group such as, for example, an ester, an amide, a cyanide, C$_{1-6}$alkylsulfonyloxy and the like groups; and eliminating the group E of the thus obtained triazinedione of formula (V). The cyclization can suitably be carried out by refluxing the intermediate (IV) in acidic medium such as acetic acid and in the presence of a base such as, for example, potassium acetate.

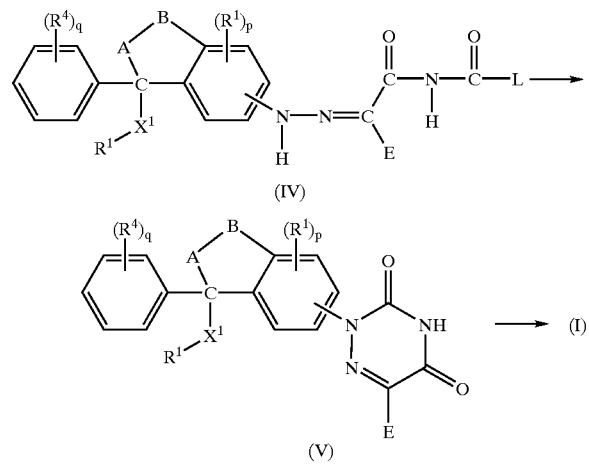

Depending on its nature, E can be eliminated using various art-known elimination procedures. For example when E is an amide or a cyano moiety, it can be hydrolized to a carboxylic moiety by for instance refluxing the intermediate bearing the E group in hydrochloric acid and acetic acid. The thus obtained intermediate can then be further reacted with mercaptoacetic acid or a functional derivative thereof to obtain a compound of formula (I). Said reaction is conveniently carried out at elevated temperatures ranging up to reflux temperature.

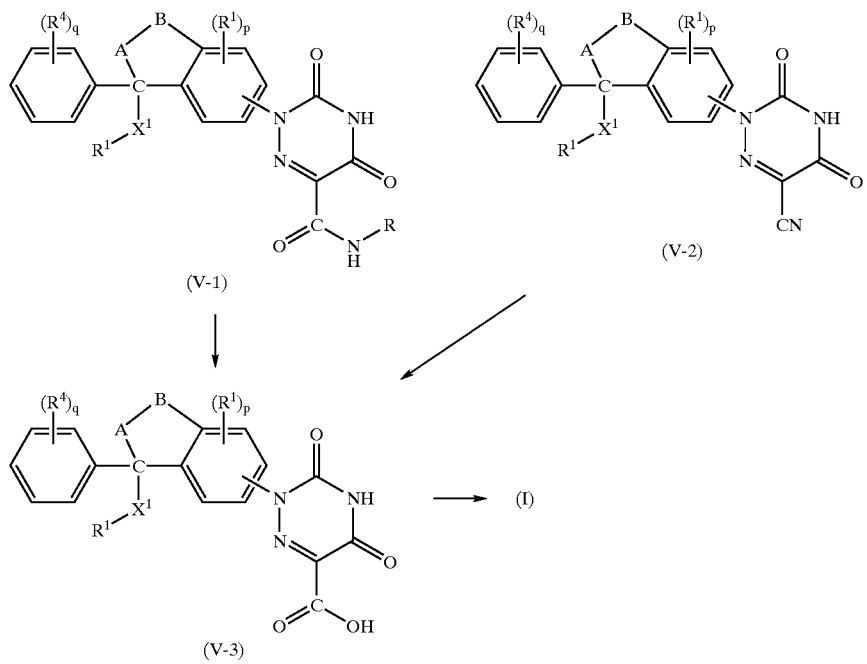

A suitable way to prepare intermediates of formula (IV) involves the reaction of an intermediate of formula (VI) with sodium nitrite or a functional derivative thereof in an acidic medium such as for example hydrochloric acid in acetic acid, and preferably in the same reaction mixture, further reacting the thus obtained intermediate with a reagent of formula (VII) wherein L and E are as defined above, in the presence of a base such as, for example, sodium acetate.

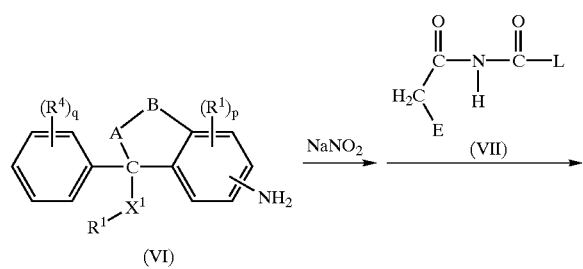

An interesting subgroup within the present invention are those compounds of formula (I) wherein —$X^1$—$R^2$ is an optionally substituted 2-thiazolyl moiety, said compounds being represented by formula (I-a). The optionally substituted 2-thiazolyl moiety can be incorporated in the compounds of formula (I-a) at different stages of the preparation process.

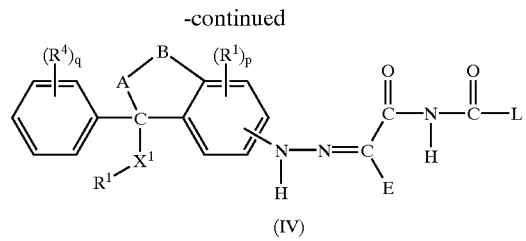

For instance, scheme 1 depicts three possible ways to prepare compounds of formula (I-a).

Scheme 1

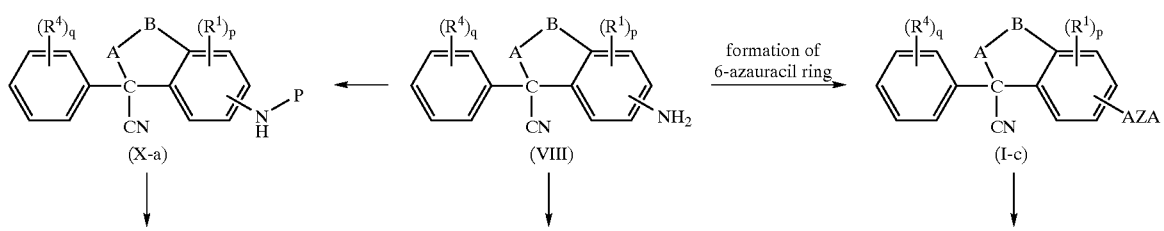

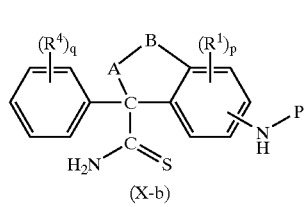 (X-b)
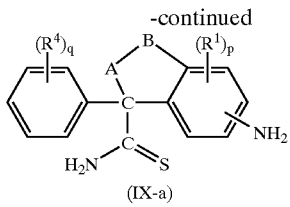 (IX-a)
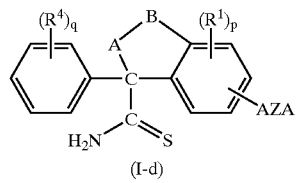 (I-d)

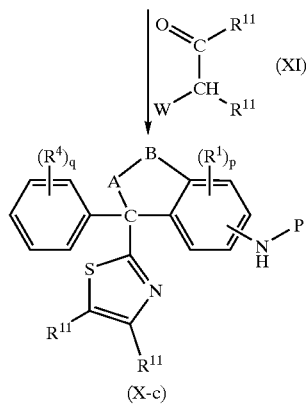 (X-c)
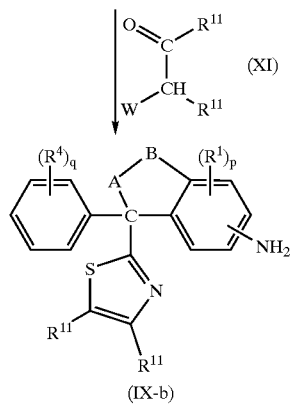 (IX-b)
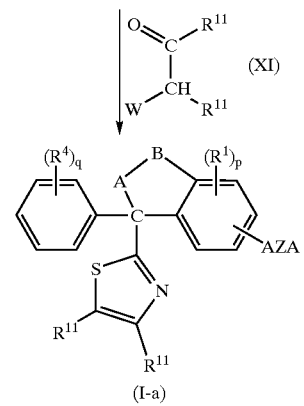 (I-a)

deprotection and formation of 6-azauracil ring formation of 6-azauracil ring

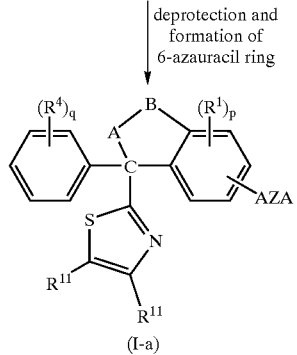 (I-a)

(I-a)

A first pathway involves the reaction of the cyano moiety in an intermediate of formula (VIII) to the corresponding thioamide using $H_2S$ gas in a suitable solvent such as, for example, pyridine and in the presence of a base such as, for example, triethylamine, thus obtaining an intermediate of formula (IX-a). This thioamide can then be cyclized with an intermediate of formula (XI) wherein W is a suitable leaving group such as, for example, a halogen, e.g. bromo, in a suitable solvent such as, for example, ethanol. The amino moiety in the resulting 2-thiazolyl derivative of formula (IX-b) can then be further reacted as described hereinabove to form a 6-azauracil ring, thus obtaining a compound of formula (I-a).

A second pathway to form compounds of formula (I-a) involves first the protecting of the amino moiety in an intermediate of formula (VIII) by introducing a suitable protective group P such as, for example, an alkylcarbonyl group, using art-known protection techniques. In the example of P being a alkylcarbonyl group, the intermediates of formula (VIII) can be reacted with the corresponding anhydride of formula alkyl—C(=O)—O—C(=O)-alkyl in an appropriate solvent such as, for example, toluene. The thus obtained intermediate of formula (X-a) can then be further reacted according to the first pathway described hereinabove. The final step, before formation of the 6-azauracil ring can be initiated after having deprotected the amino moiety using art-known deprotection techniques. In the example of P being a alkylcarbonyl group, the intermediates of formula (X-c) may be deprotected by reacting them in a suitable solvent such as, for example, ethanol, in the presence of an acid such as, for example, hydrochloric acid.

A third pathway involves first the formation of the 6-azauracil ring as described hereinabove but starting from an intermediate of formula (VIII), and subsequently reacting the thus formed compound of formula (I) wherein —$X^1$—$R^2$ is cyano, said compounds being represented by formula (I-c), with $H_2S$ and further reacting the compound of formula (I) wherein —$X^1$—$R^2$ is a thioamide, said compounds being represented by formula (I-d), with an intermediate of formula (XI) as described in the first pathway, to finally form a compound of formula (I-a).

Another interesting subgroup within the present invention are those compounds of formula (I) wherein —$X^1$—$R^2$ is an optionally substituted 1,2,4-oxadiazol-3-yl moiety, said compounds being represented by formula (I-b-1). The optionally substituted 1,2,4-oxadiazol-3-yl moiety can be incorporated at the same stages of the reaction procedure as depicted for the 2-thiazolyl derivatives in scheme 1.

For instance, analogous to one of the three pathways shown in scheme 1, compounds of formula (I-b) can be prepared by reacting an intermediate of formula (VIII) as depicted in scheme 2.

Scheme 2

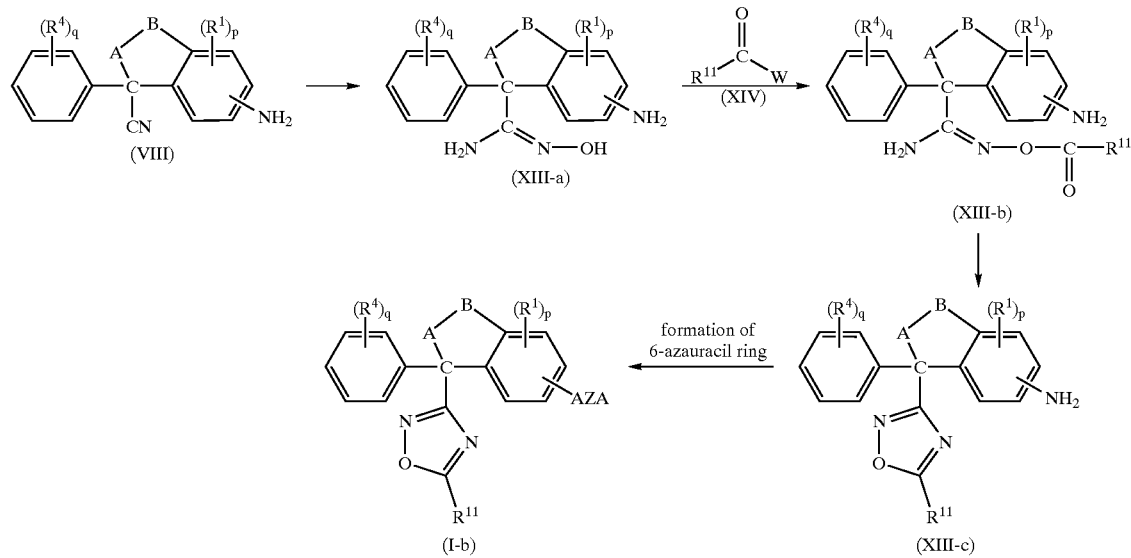

In said scheme 2, the cyano group of an intermediate of formula (VII) is reacted with hydroxylamine or a functional derivative thereof in a suitable solvent such as, for example, methanol, and in the presence of a base such as, for example, sodium methanolate. The thus formed intermediate of formula (XIII-a) is then reacted with an intermediate of formula (XIV) wherein W is a suitable leaving group such as, for example, a halogen, e.g. chloro, in an appropriate solvent such as, for example, dichloromethane, and in the presence of a base, such as, for example, N,N-(1-methylethyl) ethaneamine. The resulting intermediate of formula (XIII-b) is then cyclized to a 3-oxadiazolyl derivative of formula (XIII-c). The amino moiety in the intermediates of formula (XIII-c) can then be transformed to the 6-azauracil ring as described above.

Still another interesting subgroup within the present invention are those compounds of formula (I) wherein —X$^1$—R$^2$ is an optionally substituted 1,3,4-oxadiazol-2-yl moiety, said compounds being represented by formula (I-b-2).

For instance, compounds of formula (I-b-2) can be prepared as depicted in scheme 3.

Scheme 3

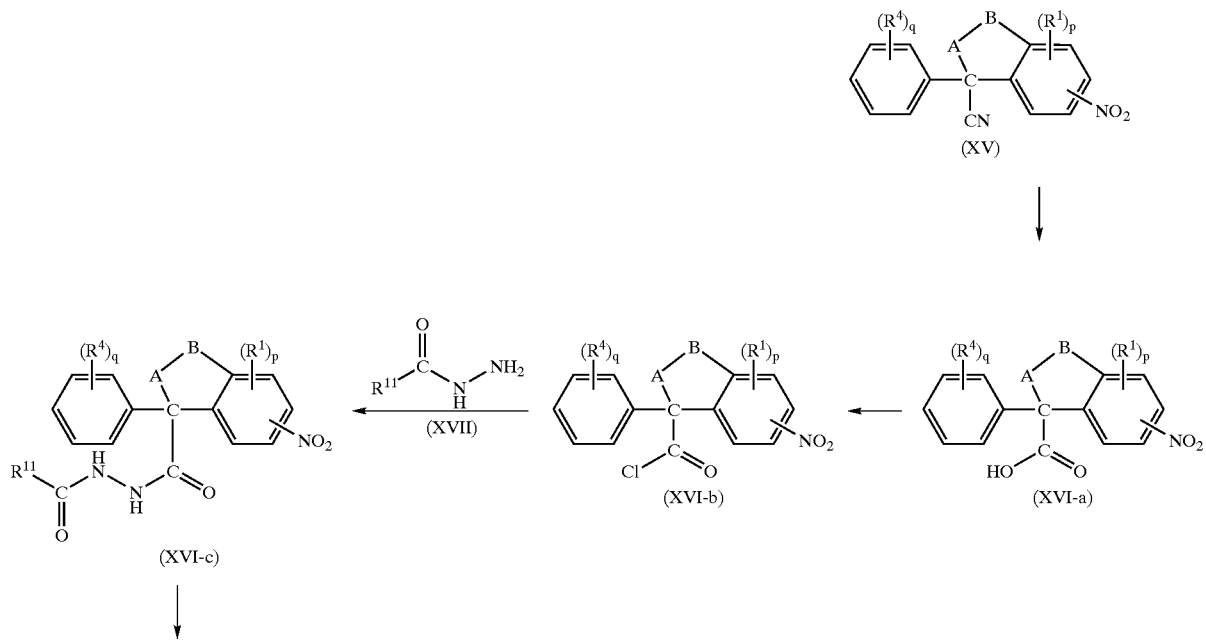

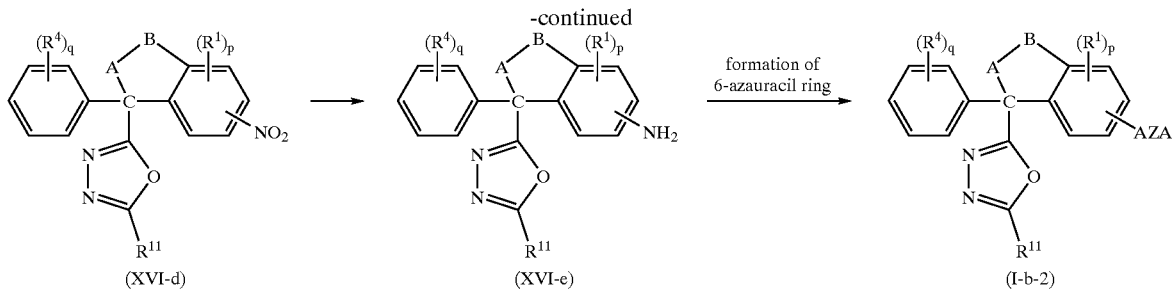

(XVI-d)          (XVI-e)          (I-b-2)

The nitrile moiety in an intermediate of formula (XV) is transformed into a carboxylic acid moiety using art-known techniques. For instance, the nitrile derivative may be refluxed in a mixture of sulfuric acid and acetic acid in water. The carboxylic acid of formula (XVI-a) may be reacted with a chlorinating agent such as, for example, thionyl chloride, to form an acylchloride derivative of formula (XVI-b). Subsequently, the acyl chloride may be reacted with a hydrazine derivative of formula (XVII) in a suitable solvent such as, for example, dichloromethane, and in the presence of a base such as, for example N,N-(1-methylethyl) ethaneamine. The thus formed intermediate of formula (XVI-c) may be cyclized to a 1,2,4-oxadiazol-2-yl derivative of formula (XVI-d) in the presence of phosphoryl chloride. As a final step before the formation of the 6-azauracil ring as described above, the nitro group in the intermediates of formula (XVI-e) is reduced to an amino group using art-known reduction techniques such as, for instance, reducing the nitro group with hydrogen in methanol and in the presence of a catalyst such as Raney Nickel.

The compounds of formula (I) can also be converted into each other following art-known procedures of functional group transformation such as, for example, those mentioned in PCT/EP98/04191 and the ones exemplified in the experimental part hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

IL-5, also known as eosinophil differentiating factor (EDF) or eosinophil colony stimulating factor (Eo-CSF), is a major survival and differentiation factor for eosinophils and therefore thought to be a key player in eosinophil infiltration into tissues. There is ample evidence that eosinophil influx is an important pathogenic event in bronchial asthma and allergic diseases such as, cheilitis, irritable bowel disease, eczema, urticaria, vasculitis, vulvitis, winterfeet, atopic dermatitis, pollinosis, allergic rhinitis and allergic conjunctivitis; and other inflammatory diseases, such as eosinophilic syndrome, allergic angiitis, eosinophilic fasciutis, eosinophilic pneumonia, PIE syndrome, idiopathic eosinophilia, eosinophilic myalgia, Crohn's disease, ulcerative colitis and the like diseases.

The present compounds also inhibit the production of other chemokines such as monocyte chemotactic protein-1 and -3 (MCP-1 and MCP-3). MCP-1 is known to attract both T-cells, in which IL-5 production mainly occurs, and monocytes, which are known to act synergetically with eosinophils (Carr et al., 1994, Immunology, 91, 3652–3656). MCP-3 also plays a primary role in allergic inflammation as it is known to mobilize and activate basophil and eosinophil leukocytes (Baggiolini et al., 1994, Immunology Today, 15(3), 127–133).

The present compounds have no or little effect on the production of other chemokines such as IL-1, IL-2, IL-3, IL-4, IL-6, IL-10, γ-interferon (IFN-γ) and granulocyte-macrophage colony stimulating factor (GM-CSF) indicating that the present IL-5 inhibitors do not act as broad-spectrum immunosuppressives.

The selective chemokine inhibitory effect of the present compounds can be demonstrated by in vitro chemokine measurements in human blood of which the test results for IL-5 are presented in the experimental part hereinafter. In vivo observations such as the inhibition of eosinophilia in mouse ear, the inhibition of blood eosinophilia in the Ascaris mouse model; the reduction of serum IL-5 protein production and splenic IL-5 mRNA expression induced by anti-CD3 antibody in mice and the inhibition of allergen- or Sephadex-induced pulmonary influx of eosinophils in guinea-pig are indicative for the usefulness of the present compounds in the treatment of eosinophil-dependent inflammatory diseases.

The present inhibitors of IL-5 production are orally active compounds.

In view of the above pharmacological properties, the compounds of formula (I) can be used as a medicine. In particular, the present compounds can be used in the manufacture of a medicament for treating eosinophil-dependent inflammatory diseases as mentioned hereinabove, more in particular bronchial asthma, atopic dertmatitis, allergic rhinitis and allergic conjunctivitis.

In view of the utility of the compounds of formula (I), there is provided a method of treating warm-blooded animals, including humans, suffering from eosinophil-dependent inflammatory diseases, in particular bronchial asthma, atopic dertmatitis, allergic rhinitis and allergic conjunctivitis. Said method comprises the systemic or topical administration of an effective amount of a compound of formula (I), a N-oxide form, a pharmaceutically acceptable addition salt or a possible stereoisomeric form thereof, to warm-blooded animals, including humans.

The present invention also provides compositions for treating eosinophil-dependent inflammatory diseases comprising a therapeutically effective amount of a compound of formula (I) and a pharmaceutically acceptable carrier or diluent.

To prepare the pharmaceutical compositions of this invention, a therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy-$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. The M.S. value can be determined by various analytical techniques, preferably, as measured by mass spectrometry, the M.S. ranges from 0.125 to 10.

The average substitution degree (D.S.) refers to the average number of substituted hydroxyls per anhydroglucose unit. The D.S. value can be determined by various analytical techniques, preferably, as measured by mass spectrometry, the D.S. ranges from 0.125 to 3.

Due to their high degree of selectivity as IL-5 inhibitors, the compounds of formula (I) as defined above, are also useful to mark or identify receptors. To this purpose, the compounds of the present invention need to be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) containing a radioactive halogen atom. In principle, any compound of formula (I) containing a halogen atom is prone for radiolabelling by replacing the halogen atom by a suitable isotope. Suitable halogen radioisotopes to this purpose are radioactive iodides, e.g. $122_I$, $123_I$, $125_I$, $131_I$; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds of formula (I) can be used in a process of specifically marking receptor sites in biological material. Said process comprises the steps of (a) radiolabelling a compound of formula (I), (b) administering this radio-labelled compound to biological material and subsequently (c) detecting the emissions from the radiolabelled compound. The term biological material is meant to comprise every kind of material which has a biological origin. More in particular this term refers to tissue samples, plasma or body fluids but also to animals, specially warm-blooded animals, or parts of animals such as organs.

The radiolabelled compounds of formula (D) are also useful as agents for screening whether a test compound has the ability to occupy or bind to a particular receptor site. The degree to which a test compound will displace a compound of formula (I) from such a particular receptor site will show the test compound ability as either an agonist, an antagonist or a mixed agonist/antagonist of said receptor.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In general, it is contemplated that a therapeutically effective daily amount would be from 0.01 mg/kg to 50 mg/kg body weight, in particular from 0.05 mg/kg to 10 mg/kg body weight. A method of treatment may also include administering the active ingredient on a regimen of between two or four intakes per day.

EXPERIMENTAL PART

PREPARATION OF THE INTERMEDIATE COMPOUNDS

EXAMPLE A1a

Preparation of

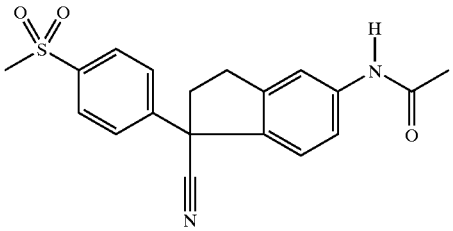

(Intermediate 1)

Sodium hydride (0.1 mol) was added portionwise at 0° C. to a solution of N-(1-cyano-2,3-dihydro-1H-inden-5-yl) acetamide (0.0499 mol) in DMF and the reaction mixture was stirred for 2 hours. 4-chlorophenyl methyl sulfone (0.1 mol) was dissolved in N,N-dimethylformamide and this solution was added dropwise to the reaction mixture. The mixture was stirred at room temperature for 1 hour. Water was added and the mixture was extracted with $CH_2Cl_2$. The separated organic layer was dried, filtered and the solvent was evaporated. The residue was purifued by short column chromatography over silica gel (eluent: $CH_2Cl_2/CH_3OH$ 98/2). The desired fractions were collected and the solvent was evaporated. The residue was crystallized from diethyl ether. The precipitate was filtered off, washed with diethyl ether and dried, yielding 14.4 g (81.4%) of intermediate 1.

EXAMPLE A1b

Preparation of

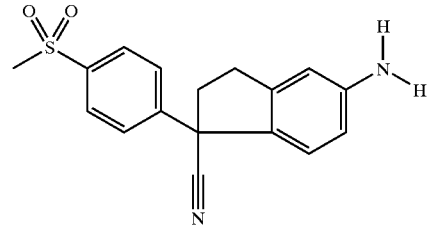

(Intermediate 2)

A suspension of intermediate (1) (0.0423 mol) in HCl 3N (150 ml) and 1,4-dioxane (150 ml) was stirred at room temperature, then heated and refluxed for 2 hours. The reaction mixture was poured out into $H_2O$ and extracted with $CH_2Cl_2$. The separated organic layer was dried, filtered, and the solvent was evaporated. The residue was stirred in diisopropyl ether. The precipitate was filtered off, washed with diisopropyl ether and dried, yielding 11.0 g (83%) of intermediate 2.

Example A1c

Preparation of

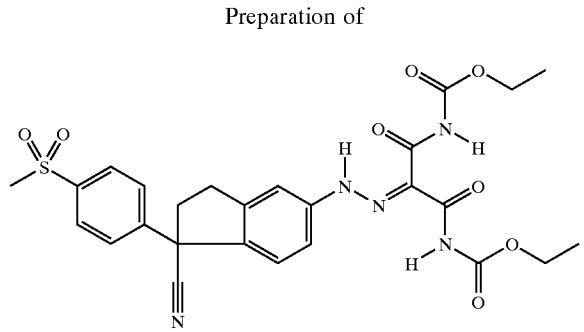

(Intermediate 3)

A solution of sodium nitrite (0.0352 mol) in water (10 ml) was added dropwise at 10° C. to a solution of intermediate (2) (0.0352 mol) and concentrated HCl (0.106 mol) in acetic acid (150 ml) and the reaction mixture was stirred for 1 hour at 10° C. A powdered mixture of sodium acetate (0.106 mol) and diethyl(1,3-dioxo-1,3-propanediyl)biscarbamate (0.0387 mol) was added. The mixture was allowed to warm to room temperature and stirred for 2 hours, then poured out onto crushed ice. The precipitate was filtered off and washed with $H_2O$. The solid was taken up in $CH_2Cl_2$. The remaining $H_2O$ was separated. The organic layer was dried, filtered and the solvent evaporated, yielding intermediate 3.

EXAMPLE A1d

Preparation of

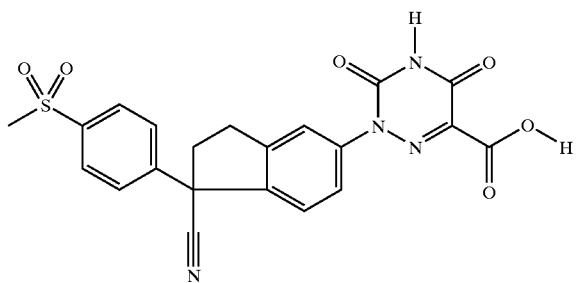

(Intermediate 4)

Concentrated HCl (10 ml) was added to a cooled mixture of intermediate (3) (0.0352 mol) in acetic acid (150 ml). The reaction mixture was stirred at 80° C. for 1 night, concentrated and co-evaporated twice with toluene, yielding intermediate 4.

PREPARATION OF THE FINAL COMPOUNDS

EXAMPLE B1a

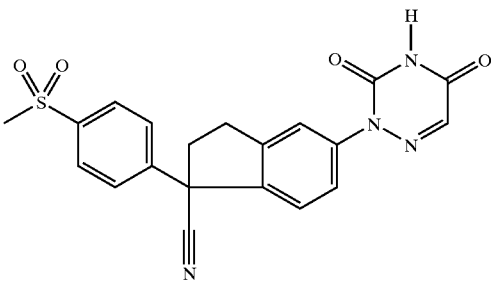

(Compound 1)

A mixture of intermediate (4) (0.0352 mol) in 2-mercaptoacetic acid (30 ml) was stirred at 180° C. for 30 minutes. The reaction mixture was poured out into water, neutralized with $NaHCO_3$ powder and extracted with $CH_2Cl_2$. The organic layer was dried, filtered and the solvent evaporated. The residue was purified by short column chromatography over silica gel (eluent: $CH_2Cl_2/CH_3OH$ 98/2). The pure fractions were collected and the solvent was evaporated. The residue was crystallized from diethyl ether. The precipitate was filtered off, washed with diethyl ether and dried, yielding 8.3 g (57%) of compound 1.

EXAMPLE B1b

Preparation of (compound 2)

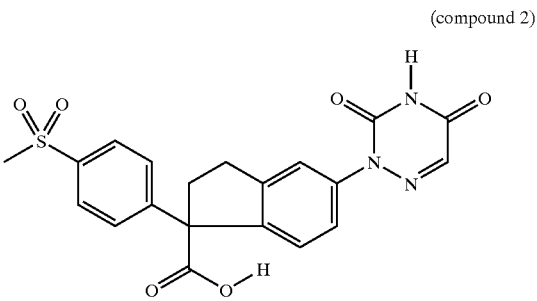

A mixture of compound 1 (0.0086 mol) in a mixture of water, acetic acid and sulfuric acid (1/1/1) (90 ml) was stirred and refluxed for 3 hours, then poured out onto crushed ice. The white precipitate was filtered off, washed with $H_2O$ and dried, yielding 3.4 g (92%) of compound 2.

EXAMPLE B1c

Preparation of (compound 3)

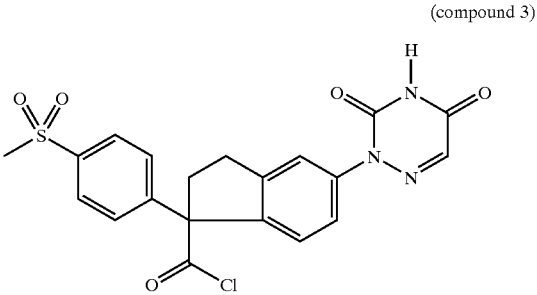

A mixture of compound 2 (0.007 mol) in thionyl chloride 50 ml) was stirred and refluxed until HCl evolution had stopped. The reaction mixture was concentrated and co-evaporated three times with toluene, yielding 3.13 g of compound 3.

EXAMPLE B1d

Preparation of (compound 4)

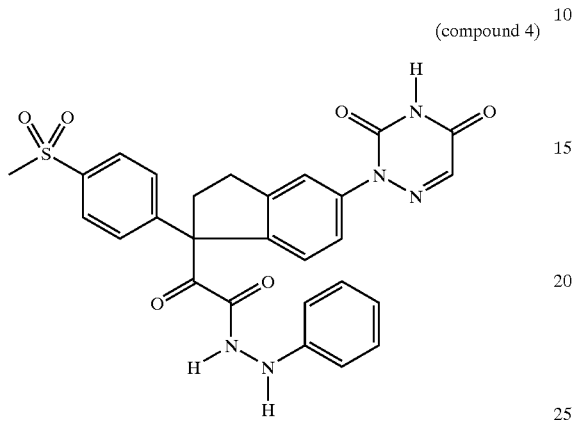

Compound 3 (0.007 mol) was added portionwise to a cooled solution of benzoic acid, hydrazide (0.0071 mol) and N-ethyldiisopropylamine (0.0071 mol) in $CH_2Cl_2$ (100 ml) and the reaction mixture was stirred at room temperature for 3 hours. $H_2O$ was added. The separated organic layer was dried, filtered and the solvent was evaporated. The residue was purified by short column chromatography over silica gel (eluent: $CH_2Cl_2/CH_3OH$ 98/2). The desired fractions were collected and the solvent was evaporated, yielding 3.6 g (94%) of compound 4.

EXAMPLE B1e

Preparation of (compound 5)

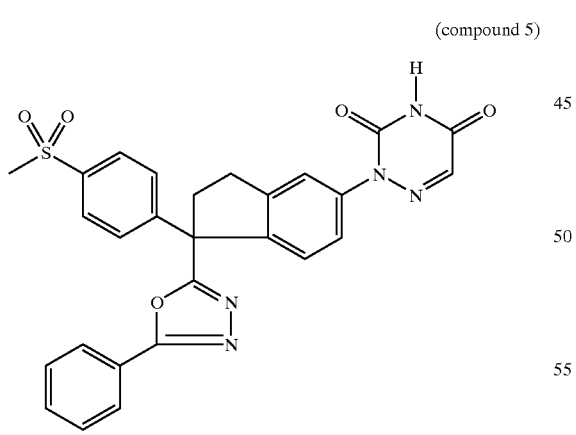

A mixture of compound 4 (0.007 mol) in phosphoryl chloride (50 ml) was stirred at 80° C. for 1 day, then stirred at room temperature, poured out onto crushed ice and extracted with $CH_2Cl_2$. The separated organic layer was dried, filtered and the solvent was evaporated. The residue was purified by short open column chromatography over silica gel (eluent: $CH_2Cl_2/CH_3OH$ 98/2). The desired fractions were collected and the solvent was evaporated. The residue was stirred in diethyl ether. The precipitate was filtered off, washed with diethyl ether and dried, yielding 0.84 g (22%) of compound 5.

EXAMPLE B2a

Preparation of (compound 6)

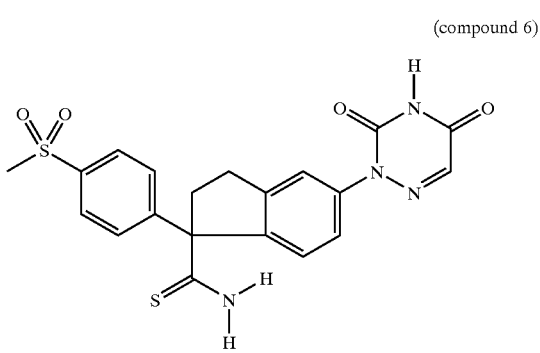

A solution of compound 1 (0.00735 mol) in pyridine (50 ml) and N-ethyldiisopropylamine (4 ml) was stirred at 80° C. Pyridine was allowed to bubble through this solution for 12 hours. The solvent was evaporated and the residue was co-evaporated twice with toluene. The residue was taken up in $CH_2Cl_2$, washed with HCl 3N, dried, filtered, and the solvent was evaporated. The residue was boiled in ethanol, filtered off and dried, yielding 2.0 g (62%) of compound 6. The filtrate stood over the weekend. The formed precipitate was filtered off, washed with ethanol and diisopropyl ether, and dried, yielding 0.4 g (13%) of compound 6.

EXAMPLE B3b

Preparation of (compound 7)

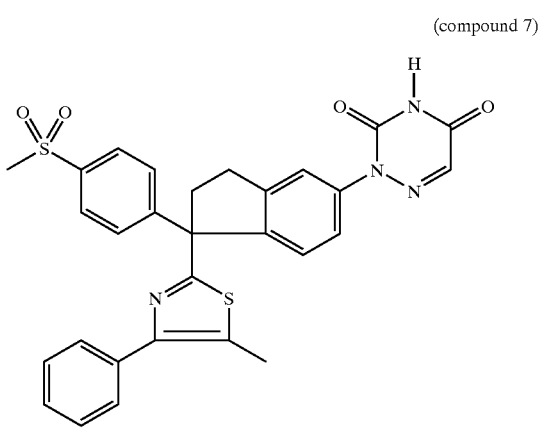

A mixture of compound 6 (0.00452 mol) and 2-bromopropiophenone (0.005 mol) in ethanol (17 ml) and N,N-dimethylformamide (10 ml) was stirred over the weekend at room temperature under $N_2$ atmosphere. Some more bromopropiophenone (0.00136 mol) was added and the reaction mixture was stirred overnight at 40° C. The solvent was evaporated and ethylacetate was added. The mixture was washed with brine, dried, filtered and the solvent was evaporated. The residue was purified by column chromatography over silica gel (eluent: $CH_2Cl_2/CH_3OH$ 100/0 to 98/2). The desired fractions were collected and the solvent was evaporated. The residue was crystallized from ethanol. The precipitate was filtered off and dried, yielding compound 7 (fraction 1). The filtrate was evaporated and the residue was crystallized from ethanol. The precipitate was filtered off and dried, yielding compound 7 (fraction 2). Fractions 1 and 2 were combined and recrystallized from ethanol. The precipitate was filtered off, washed with diisopropyl ether and dried, yielding 1 g (40%) of compound 7.

C. PHARMACOLOGICAL EXAMPLE

EXAMPLE C.1 in vitro Inhibition of IL-5 Production in Human Blood

Human Whole Blood Stimulation

Peripheral blood from healthy male donors was drawn into heparinized syringes (12.5 U heparin/ml). Blood samples were three-fold diluted in RMPI 1640 medium (Life Technologies, Belgium) supplemented with 2 mM L-glutamine, 100 U/ml penicillin and 100 mg/ml streptomycin, and 300 ml fractions were distributed in 24-well multidisc plates. Blood samples were preincubated (60 minutes at 37° C.) in a humidified 6% $CO_2$-atmosphere with 100 ml of drug solvent (final concentration 0.02% dimethylsulfoxide in RPMI 1640) or with 100 ml of an appropriate dose of test compound before being stimulated by the addition of 100 ml of phytohemagglutinin HA17 (Murex, UK) at a final concentration of 2 mg/ml. After 48 hours, cell-free supernatant fluids were collected by centrifugation and stored at −70° C. until tested for the presence of IL-5.

IL-5 Measurements

IL-5 measurements were conducted as described in Van Wauwe et al. (1996, Inflamm Res, 45, 357–363) on page 358 using ELISA.

Table 1 lists the percentage inhibition of IL-5 production (column "% inh") at a test dose of $1\times10^{-6}$ M for the compounds of the present invention.

TABLE 1

| Co. No. | % inh. |
|---------|--------|
| 6       | 6      |
| 7       | 39     |

D. COMPOSITION EXAMPLES

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

EXAMPLE D.1

Film-coated Tablets

Preparation of Tablet Core

A mixture of A.I. (100 g), lactose (570 g) and starch (200 g) was mixed well and thereafter humidified with a solution of sodium dodecyl sulfate (5 g) and polyvinylpyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinylpyrrolidone (5 g) and concentrated color suspension (30 ml) and the whole was homogenated. The tablet cores were coated with the thus obtained mixture in a coating apparatus.

EXAMPLE D. 2

2% Topical Cream

To a solution of hydroxypropyl b-cyclodextrine (200 mg) in purified water is added A.I. (20 mg) while stirring. Hydrochloric acid is added until complete dissolution and next sodium hydroxide is added until pH 6.0. While stirring, glycerol (50 mg) and polysorbate 60 (35 mg) are added and the mixture is heated to 70° C. The resulting mixture is added to a mixture of mineral oil (100 mg), stearyl alcohol (20 mg), cetyl alcohol (20 mg), glycerol monostearate (20 mg) and sorbate 60 (15 mg) having a temperature of 70° C. while mixing slowly. After cooling down to below 25° C., the rest of the purified water q.s. ad 1 g is added and the mixture is mixed to homogenous.

What is claimed is:

1. A compound of formula (I)

a N-oxide, a pharmaceutically acceptable addition salt or a stereochemically isomeric forms thereof, wherein:

p represents an integer being 0, 1, 2 or 3;

q represents an integer being 0, 1, 2, 3, 4 or 5;

—A—B— represents —$(CH_2)_r$—, —$(CH_2)_t$—O—, —$(CH_2)_t$—S(=O)$_u$— or —$(CH_2)_t$—$NR^3$—;

r represents 2, 3 or 4;

each t independently represents 1, 2 or 3;

u represents 0, 1 or 2;

$X^1$ represents O, S, $NR^3$ or a direct bond;

each $R^1$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, $Het^3$, $R^6$, $NR^7R^8$ or $C_{1-4}$alkyl substituted with $Het^3$, $R^6$ or $NR^7R^8$;

$R^2$ represents aryl, $Het^1$, $C_{3-7}$cycloalkyl, cyano, $C_{1-6}$alkyl, —C(=Q)—$X^2$—$R^{15}$ or $C_{1-6}$alkyl substituted with one or two substituents selected from hydroxy, cyano, amino, mono-or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$, $Het^1$oxy, $Het^1$thio and —C(=Q)—$X^2$—$R^{15}$;

$R^3$ represents hydrogen or $C_{1-4}$alkyl;

each $R^4$ independently represents $C_{1-6}$alkyl, halo, polyhalo$C_{1-6}$alkyl, hydroxy, mercapto, $C_{1-6}$alkyloxy, $C_{1-6}$alkylthio, $C_{1-6}$alkylcarbonyloxy, aryl, cyano, nitro, Het³, R⁶, NR⁷R⁸ or $C_{1-4}$alkyl substituted with Het³, R⁶ or NR⁷R⁸;

each R¹⁵ independently represents hydrogen, $C_{1-6}$alkyl, $C_{3-7}$cycloalkyl, aryl or $C_{1-6}$alkyl substituted with aryl, halo, hydroxy or Het¹;
where X² is a direct bond, R¹⁵ may also be halo or Het¹;
where X² is NR₅, R¹⁵ may also be hydroxy;
where X² is C(=O)—NH—NH or NH—NH—C(=O), R¹⁵ may be replaced by R¹¹;

R⁵ represents hydrogen, $C_{1-6}$alkyl, $C_{1-6}$alkyloxy or aryl$C_{1-6}$alkyl;

each Q independently represents O, S or NR₃;

each X² independently represents O, S, NR₅, C(=O)—NH—NH, NH—NH—C(=O) or a direct bond;

each R⁶ independently represents $C_{1-6}$alkylsulfonyl, aminosulfonyl, mono- or di—($C_{1-4}$alkyl)aminosulfonyl, mono- or di(benzyl)aminosulfonyl, polyhalo$C_{1-6}$alkylsulfonyl, $C_{1-6}$alkylsulfinyl, phenyl$C_{1-4}$alkylsulfonyl, piperazinylsulfonyl, aminopiperidinylsulfonyl, piperidinylaminosulfonyl, N—$C_{1-4}$alkyl-N-piperidinylaminosulfonyl or mono-or di($C_{1-4}$alkyl)amino$C_{1-4}$alkylsulfonyl;

each R⁷ and each R⁸ are independently selected from hydrogen, $C_{1-4}$alky), hydroxy-$C_{1-4}$alkyl, dihydroxy $C_{1-4}$alkyl, aryl, aryl$C_{1-4}$alkyl, $C_{1-4}$alkyloxy$C_{1-4}$alkyl, $C_{1-4}$alkylcarbonyl, aminocarbonyl, arylcarbonyl, Het³carbonyl, $C_{1-4}$alkylcarbonyloxy-$C_{1-4}$alkylcarbonyl, hydroxy$C_{1-4}$alkylcarbonyl, $C_{1-4}$alkyloxycarbonylcarbonyl, mono- or di($C_{1-4}$alkyl)amino$C_{1-4}$alkyl, arylaminocarbonyl, arylaminothiocarbonyl, Het³aminocarbonyl, Het³aminothiocarbonyl, $C_{3-7}$cycloalkyl, pyridinyl $C_{1-4}$alkyl, $C_{1-4}$alkanediyl-C(=O)—O—R¹⁴, —C(=O)—O—R¹⁴, —Y—$C_{1-4}$alkanediyl-C(=O)—O—R¹⁴, Het³ and R⁶;

Y represents O, S, NR₃, or S(O)₂;

R⁹ and R¹⁰ are each independently selected from hydrogen, $C_{1-4}$alkyl, hydroxy$C_{1-4}$alkyl, dihydroxy $C_{1-4}$alkyl, phenyl, pheny$C_{1-4}$alkyl, $C_{1-4}$alkyloxy $C_{1-4}$alkyl, $C_{1-4}$alkylcarbonyl, aminocarbonyl, phenylcarbonyl, Het³carbonyl, $C_{1-4}$alkylcarbonyloxy$C_{1-4}$alkylcarbonyl, hydroxy $C_{1-4}$alkylcarbonyl, $C_{1-4}$alkyloxycarbonylcarbonyl, mono- or di($C_{1-4}$alkyl)amino$C_{1-4}$alkyl, phenylaminocarbonyl, phenylaminothiocarbonyl, Het³aminocarbonyl, Het³aminothiocarbonyl, $C_{3-7}$cycloalkyl, pyridinyl$C_{1-4}$ alkyl, $C_{1-4}$alkanediyl—C(=O)—O—R¹⁴, —C(=O)—O—R¹⁴, —Y—$C_{1-4}$alkanediyl—C(=O)—O—R¹⁴, Het³ R₆;

each R₁₁ independently being selected from hydroxy, mercapto, cyano, nitro, halo, trihalomethyl, $C_{1-4}$alkyloxy, formyl, trihalo$C_{1-4}$alkylsulfonyloxy, R⁶, NR⁷R⁸, C(=O)NR⁷R⁸, —C(=O)—O—R¹⁴, —Y—$C_{1-4}$alkanediyl—C(=O)—O—R¹⁴, aryl, aryloxy, arylcarbonyl, $C_{3-7}$cycloalkyl, $C_{3-7}$cycloalkyloxy, phthalimide-2-yl, Het³, Het⁴ and C(=O)Het³;

R¹² and R¹³ are each independently selected from hydrogen, $C_{1-4}$alkyl, hydroxy$C_{1-4}$alkyl, dihydroxyc $C_{1-4}$alkyl, phenyl, phenyl$C_{1-4}$alkyl, $C_{1-4}$alkyloxy $C_{1-4}$alkyl, $C_{1-4}$alkylcarbonyl, phenylcarbonyl, $C_{1-4}$alkylcarbonyloxy$C_{1-4}$alkylcarbonyl, hydroxy $C_{1-4}$alkylcarbonyl, $C_{1-4}$alkyloxycarbonylcarbonyl, mono- or di ($C_{1-4}$alkyl)amino$C_{1-4}$alkyl, phenylamino-carbonyl, phenylaminothiocarbonyl, $C_{3-7}$cycloalkyl, pyridinyl$C_{1-4}$alkyl, $C_{1-4}$alkanediyl-C(=O)—O—R¹⁴, —C(=O)—O—R¹⁴, —Y—$C_{1-4}$alkanediyl—C(=O)—O—R¹⁴ and R⁶;

each R¹⁴ independently represents hydrogen, $C_{1-4}$alkyl, $C_{3-7}$cycloalkyl, aminocarbonylmethylene, mono-or di($C_{1-4}$alkyl)aminocarbonylmethylene, mono-or di($C_{3-7}$cycloalkyl)aminocarbonylmethylene, azetidin-1-ylcarbonylmethylene, pyrrolidin-1-ylcarbonylmethylene, piperidin-1-ylcarbonylmethylene or homopiperidin-1-ylcarbonylmethylene;

aryl represents phenyl optionally substituted with one, two or three substituents each independently selected from nitro, azido, cyano, halo, hydroxy, $C_{1-4}$alkyl, $C_{3-7}$cyclo-alkyl, $C_{1-4}$alkyloxy, formyl, polyhalo $C_{1-4}$alkyl, NR⁹R¹⁰, C(=O)NR⁹R¹⁰, C(=O)—O—R¹⁴, R₆, —O—R⁶, phenyl, Het³, C(=O)Het³ and $C_{1-4}$alkyl substituted with hydroxy, $C_{1-4}$alkyloxy, C(=O)—O—R¹⁴, —Y—$C_{1-4}$alkanediyl—C(=O)—O—R¹⁴, Het³ or NR⁹R¹⁰;

Het represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, pyrrolidinyl, piperidinyl, piperazinyl, morpholinyl, thiomorpholinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from Het², R¹¹ and $C_{1-4}$alkyl optionally substituted with one or two substituents independently selected from Het² and R¹¹;

Het² represents a heterocycle selected from pyrrolyl, pyrrolinyl, imidazolyl, imidazolinyl, pyrazolyl, pyrazolinyl, triazolyl, tetrazolyl, furanyl, tetrahydrofuranyl, thienyl, thiolanyl, dioxolanyl, oxazolyl, oxazolinyl, isoxazolyl, thiazolyl, thiazolinyl, isothiazolyl, thiadiazolyl, oxadiazolyl, pyridinyl, pyrimidinyl, pyrazinyl, pyranyl, pyridazinyl, dioxanyl, dithianyl, trithianyl, triazinyl, benzothienyl, isobenzothienyl, benzofuranyl, isobenzofuranyl, benzothiazolyl, benzoxazolyl, indolyl, isoindolyl, indolinyl, purinyl, 1H-pyrazolo[3,4-d]pyrimidinyl, benzimidazolyl, quinolyl, isoquinolyl, cinnolinyl, phtalazinyl, quinazolinyl, quinoxalinyl, thiazolopyridinyl, oxazolopyridinyl and imidazo[2,1-b]thiazolyl; wherein said heterocycles each independently may optionally be substituted with one, or where possible, two or three substituents each independently selected from R¹¹ and $C_{1-4}$alkyl optionally substituted with one or two substituents independently selected from R¹¹;

Het³ represents a monocyclic heterocycle selected from pyrrolidinyl, piperidinyl, piperazinyl, morpholinyl, thiomorpholinyl and tetrahydropyranyl; wherein said monocyclic heterocycles each independently may optionally be substituted with, where possible, one, two, three or four substituents each independently selected from hydroxy, $C_{1-4}$alkyl, $C_{1-4}$alkyloxy, $C_{1-4}$alkylcarbonyl, piperidinyl, $NR^{12}R^{13}$, $C(=O)-O-R^{14}$, $R^6$ and $C_{1-4}$alkyl substituted with one or two substituents independently selected from hydroxy, $C_{1-4}$alkyloxy, phenyl, $C(=O)-O-R^{14}$, $-Y-C_{1-4}$alkanediyl$-C(=O)-O-R^{14}$, $R^6$ and $NR^{12}R^{13}$;

$Het^4$ represents a monocyclic heterocycle selected from pyrrolyl, imidazolyl, pyrazolyl, triazolyl, tetrazolyl, furanyl, thienyl, oxazolyl, isoxazolyl, thiazolyl, isothiazolyl, thiadiazolyl, oxadiazolyl, pyridinyl, pyrimidinyl, pyrazinyl, pyranyl, pyridazinyl and triazinyl.

2. A compound as claimed in claim 1 wherein the 6-azauracil moiety is connected to the annelated phenyl ring in the 2 or 3 position.

3. A compound as claimed in claim 2 wherein $Het^1$, cyano, $-C(=Q)-X^2-R^{15}$ or $C_{1-6}$alkyl substituted with one or two substituents selected from hydroxy, cyano, $-C(=Q)-X^2-R_{15}$, amino, mono- or di($C_{1-4}$alkyl)amino, $C_{1-6}$alkyloxy, $C_{1-6}$alkylsulfonyloxy, $C_{1-6}$alkyloxycarbonyl, $C_{3-7}$cycloalkyl, aryl, aryloxy, arylthio, $Het^1$oxy and $Het^1$thio.

4. A compound as claimed in claim 3 wherein wherein $-A-B-$ is $(CH_2)_r$.

5. A compound as claimed in claim 4 wherein p is 0 and q is 0 or 1.

6. A composition comprising a pharmaceutically acceptable carrier and, as active ingredient, a therapeutically effective amount of a compound as claimed in claim 1.

7. A process for preparing a composition comprising mixing a pharmaceutically acceptable carrier with a therapeutically effective amount of a compound of claim 1.

8. A method for treating eosinophil-dependent inflammatory diseases in a warm-blooded animal in need thereof comprising administering to the warm-blooded animal a therapeutically effective amount of a compound of claim 1.

* * * * *